Figure 1A:
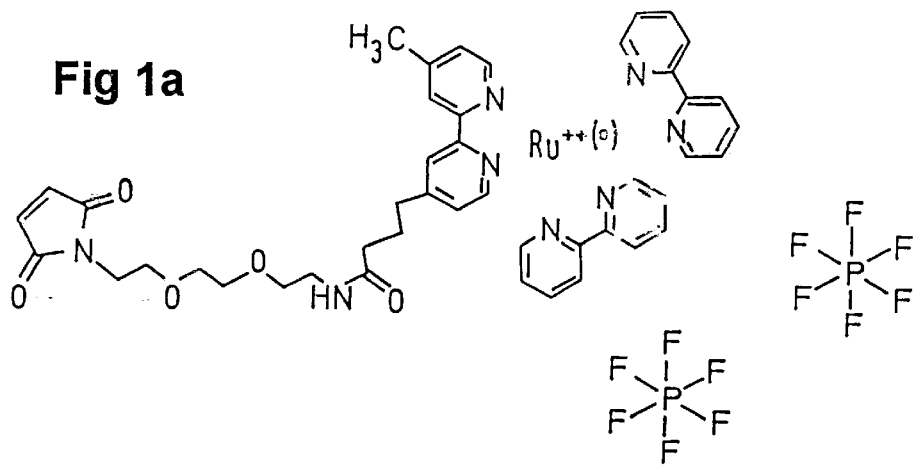

United States Patent [19]
Herrmann et al.

[11] Patent Number: 5,981,286
[45] Date of Patent: *Nov. 9, 1999

[54] HYDROPHILIC METAL COMPLEXES

[75] Inventors: Rupert Herrmann; Hans-Peter Josel, both of Weilheim; Gunter Pappert, Starnberg; Fritz Vögtle, Alfter-Impekoven; Bruno Frommberger, Bonn; Jörg Issberner, Swisttal, all of Germany

[73] Assignee: Roche Diagnostics, GmbH, Mannheim, Germany

[*] Notice: This patent is subject to a terminal disclaimer.

[21] Appl. No.: 08/765,452

[22] PCT Filed: Jul. 24, 1995

[86] PCT No.: PCT/EP95/02923

§ 371 Date: Jan. 16, 1997

§ 102(e) Date: Jan. 16, 1997

[87] PCT Pub. No.: WO96/03410

PCT Pub. Date: Feb. 8, 1996

[30] Foreign Application Priority Data

Jul. 25, 1994 [DE] Germany ............... 44 26 276
Aug. 31, 1994 [DE] Germany ............... 44 30 998
Nov. 4, 1994 [DE] Germany ............... 44 39 346

[51] Int. Cl.$^6$ ............... G01N 33/20; G01N 21/76; C07F 15/00; C09K 11/06
[52] U.S. Cl. ............... 436/84; 436/92; 436/172; 436/800; 546/10; 556/136; 252/301.16; 252/301.33

[58] Field of Search ............... 436/172, 518, 436/800, 84, 92; 556/136; 252/700, 301.16, 301.33, 301.4 R; 546/10

[56] References Cited

U.S. PATENT DOCUMENTS

| 4,745,076 | 5/1988 | Muller et al. ............... 436/537 |
| 5,075,447 | 12/1991 | Muller et al. ............... 546/10 |
| 5,238,808 | 8/1993 | Bard et al. ............... 435/4 |

FOREIGN PATENT DOCUMENTS

| 86/02734 | 5/1986 | WIPO . |
| 87/06706 | 11/1987 | WIPO . |
| 92/14139 | 8/1992 | WIPO . |

OTHER PUBLICATIONS

Journal of the American Chemical Society, vol. 116, No. 8, Apr. 20, 1994, pp. 3399–3404, Seiler, M. et al, "Photoinduced Electron Transfer in Supramolecular Assemblies Composed of . . . ".

Chemical Abstracts, vol. 98, No. 22, May 30, 1993, abstract No. 188896x, Markovitsi, D., et al, "Annelides. VI. Photochemical Properties of Micellar Phases of Metal Ion Complexes" p. 587; pp. 531–537.

Primary Examiner—Donald E. Adams
Assistant Examiner—P. Ponnaluri
Attorney, Agent, or Firm—Nikaido Marmelstein Murray & Oram, LLP.

[57] ABSTRACT

The present invention concerns new hydrophilic metal complexes and their use as luminescent marker groups in immunoassays.

18 Claims, 11 Drawing Sheets

INSTEAD OF ETHYLENE - PROPYLENE BRIDGES ARE ALSO TO BE INSERTED INTO THE SPACER $Y' = O, NH, S$

INSTEAD OF BIPYRIDINE PHENANTHROLINE IS ALSO TO BE INSERTED (BROKEN LINES)

$n' = 1-10$
$R' = H, C_1-C_5$-ALKYL
X= FUNCTIONAL REACTIVE OR ACTIVATABLE GROUP

INSTEAD OF ETHYLENE - PROPYLENE BRIDGES ARE ALSO TO BE INSERTED INTO THE SPACER $Y' = O, NH, S$

INSTEAD OF BIPYRIDINE PHENANTHROLINE IS ALSO TO BE INSERTED (BROKEN LINES)

$n' = 1-10$
$R' = H, C_1-C_5$-ALKYL
X = FUNCTIONAL REACTIVE OR ACTIVATABLE GROUP

INSTEAD OF ETHYLENE - PROPYLENE BRIDGES ARE ALSO TO BE INSERTED INTO THE SPACER

Y'= O, NH, S

INSTEAD OF BIPYRIDINE PHENANTHROLINE IS ALSO TO BE INSERTED (BROKEN LINES)

n'=1-10
R'=H, $C_1$-$C_5$-ALKYL
X= FUNCTIONAL REACTIVE OR ACTIVATABLE GROUP

DIAGRAM II

REACTION DIAGRAM III

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Asn Asn Thr Arg Lys Ser Ile Ser Ile Gly Pro Gly Arg Ala Phe Tyr
1               5                   10                  15

Thr
```

(2) INFORMATION FOR SEQ ID NO:2:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Asn Thr Thr Arg Ser Ile Ser Ile Gly Pro Gly Arg Ala Phe Tyr
1               5                   10                  15
```

(2) INFORMATION FOR SEQ ID NO:3:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

```
Ile Asp Ile Gln Glu Glu Arg Arg Met Arg Ile Gly Pro Gly Met Ala
1               5                   10                  15

Trp Tyr Ser
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Ala Val Glu Arg Tyr Leu Lys Asp Gln Gln Leu Leu Gly Ile Trp
1               5                  10                  15
```

(2) INFORMATION FOR SEQ ID NO:5:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Gln Ala Arg Ile Leu Ala Val Glu Arg Tyr Leu Lys Asp Gln Gln Leu
1               5                  10                  15
Leu Gly Ile Trp Gly Ala Ser Gly
            20
```

(2) INFORMATION FOR SEQ ID NO:6:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Trp Gly Ile Arg Gln Leu Arg Ala Arg Leu Leu Ala Leu Glu Thr Leu
1               5                  10                  15
Leu Gln Asn
```

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Leu Gly Ile Trp Gly Cys Ser Gly Lys Leu Ile Cys Thr Thr Ala Val
1               5                  10                  15
```

(2) INFORMATION FOR SEQ ID NO:8:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Gly Cys Ser Gly Lys Leu Ile Cys Thr Thr Ala Val Pro Trp Asn Ala
1               5                   10                  15
Ser Trp Ser
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Lys Asp Gln Gln Leu Leu Gly Ile Trp Gly Ser Ser Gly Lys Leu
1               5                   10                  15
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Ala Leu Glu Thr Leu Leu Gln Asn Gln Leu Leu Ser Leu Trp
1               5                   10
```

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Asn Ser Trp Gly Cys Ala Phe Arg Gln Val Cys His Thr Thr
1               5                   10
```

(2) INFORMATION FOR SEQ ID NO:12:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Gln Ala Gln Leu Asn Ser Trp Gly Cys Ala Phe Arg Gln Val Cys His
1               5                   10                  15
Thr Thr Val Pro Trp Pro Asn Asp Ser Leu Thr
            20                  25
```

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:13:

Lys Asn Lys Arg Asn Thr Asn Arg Arg
1               5

(2) INFORMATION FOR SEQ ID NO:14:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Lys Asn Lys Arg Asn Thr Asn Arg Arg Pro Gln Asp Val Lys Phe Pro
1               5                   10                  15

Gly Gly Gly Gln Ile Val Gly Gly Val
            20                  25

(2) INFORMATION FOR SEQ ID NO:15:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Ser Gln His Leu Pro Tyr Ile Glu Gln Gly Leu Ala Glu Gln Phe Lys
1               5                   10                  15

Gln Gln Ala Leu Gly Leu Leu Gln Thr
            20                  25

(2) INFORMATION FOR SEQ ID NO:16:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Ser Arg Gly Asn His Val Ser Pro Thr His Tyr Val Pro Glu Ser Asp
1               5                   10                  15

Ala Ala (2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Ser Arg Arg Phe Ala Gln Ala Leu Pro Val Trp Ala Arg Pro Asp
1               5                   10                  15

(2) INFORMATION FOR SEQ ID NO:18:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Lys Asn Lys Arg Asn Thr Asn Arg Arg Pro Gln Asp Val Lys Phe Pro
1               5                  10                  15
Gly Gly Gly Gln Ile Val Gly Gly Val Leu Leu Pro Arg Arg
            20                  25                  30
```

(2) INFORMATION FOR SEQ ID NO:19:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Asn Pro Lys Pro Gln Lys Lys Asn Lys Arg Asn Thr Asn Arg Arg
1               5                  10                  15
```

(2) INFORMATION FOR SEQ ID NO:20:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Gly Gln Ile Val Gly Gly Val Tyr Leu Leu Pro Arg Arg Gly Pro Arg
1               5                  10                  15
Leu Gly
```

(2) INFORMATION FOR SEQ ID NO:21:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Pro Gln Asp Val Lys Phe Pro Gly Gly Gly Gln Ile Val Gly Gly Val
1               5                  10                  15
```

(2) INFORMATION FOR SEQ ID NO:22:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Ser Arg Gly Asn His Val Ser Pro Thr His Tyr Val Pro Glu Ser Asp
1               5                   10                  15

Ala Ala (2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Ser Gln His Leu Pro Tyr Ile Glu Gln
1               5

HYDROPHILIC METAL COMPLEXES

The present invention concerns new hydrophilic metal complexes and their use as luminescent marker groups in immunoassays.

Luminescent metal complexes are known from the state of the art. EP-A-0 178 450 discloses ruthenium complexes that are coupled to an immunologically active material in which the ruthenium complexes contain three identical or different bicyclic or polycyclic ligands with at least two nitrogen-containing heterocycles and at least one of these ligands is substituted with at least one water-solubilizing group such as —$SO_3H$ or —COOH and at least one of these ligands is substituted directly or via a spacer group with at least one reactive group such as —COOH and the ligands are bound via nitrogen atoms to the ruthenium.

EP-A-0 580 979 discloses the use of osmium or ruthenium complexes as marker groups for electrochemiluminescence. Heterocycles containing nitrogen such as bipyridines are mentioned as ligands for these complexes. WO 87/06706 discloses further metal complexes which are suitable as marker groups for electrochemiluminescence measurements.

The disadvantages of the known metal complexes of the state of the art are a poor quantum yield in electrochemiluminescence measurements due to oxygen quenching and photodissociation or/and a high unspecific binding to proteins.

Therefore the object underlying the present invention was to at least partially eliminate the disadvantages of they state of the art.

Surprisingly it was found that the introduction of $C_2$–$C_3$ alkyleneoxy, $C_2$–$C_3$ alkylenethio or/and $C_2$–$C_3$ alkyleneamino units and in particular ethylene glycol or/and propylene glycol units into luminescent metal complexes reduces the adsorption of conjugates of these complexes with an immunologically reactive substance and thus also improves the stability and recovery of the conjugates in immunoassays. Moreover an increased quantum yield can be achieved.

In addition it was found that the properties of metal complexes can also be improved by introducing polyhydroxy units. These polyhydroxy units can be extended to form dendrimer-like structures with several generations. Moreover incorporation of polyamine structures enables the electron donor required for electrochemiluminescence measurements to be integrated directly into the ligand sphere of the complex.

A further improvement according to the invention concerns metal complexes in the form of a cage or semi-cage in which the ligands are linked together singly or multiply preferably via hydrophilic spacers. This also leads to a substantial improvement of the photostability and to a reduction of the oxygen quenching.

One subject matter of the present invention is thus a metal complex of the general formula (I):

$$[M(L_1L_2L_3)_n]-X_mA \qquad (I)$$

in which M is a divalent or trivalent metal cation selected from rare earth or transition metal ions, $L_1$, $L_2$ and $L_3$ are the same or different and denote ligands with at least two nitrogen-containing heterocycles wherein $L_1$, $L_2$ and $L_3$ are bound to the metal cation via nitrogen atoms, X is a reactive or activatable functional group which is covalently bound to at least one of the ligands $L_1$, $L_2$ and $L_3$, n is an integer from 1 to 10, m is an integer from 1 to 6 and is preferably 1 to 3 and A denotes one or several negatively charged groups that are required to balance the charge wherein the complex contains at least one hydrophilic group selected from $C_2$–$C_3$ alkyleneoxy units, $C_2$–$C_3$ alkylenethio units, $C_2$–$C_3$ alkyleneamino units and polyhydroxy units.

The metal complex is preferably a luminescent metal complex i.e. a metal complex which can generate a detectable luminescence reaction. This luminescence reaction can for example be detected by fluorescence or by electrochemiluminescence measurement. The metal cation in this complex is for example a transition metal or a rare earth metal. The metal is preferably ruthenium, osmium, rhenium, iridium, rhodium, platinum, indium, palladium, molybdenum, technetium, copper, chromium or tungsten. Ruthenium, iridium, rhenium, chromium and osmium are particularly preferred. Ruthenium is most preferred.

The ligands $L_1$, $L_2$ and $L_3$ are ligands containing at least two nitrogen-containing heterocycles. Aromatic heterocycles are preferred such as bipyridyl, bipyrazyl, terpyridyl and phenanthrolyl. The ligands $L_1$, $L_2$ and $L_3$ are particularly preferably selected from bipyridine and phenanthroline ring systems.

The reactive or activatable functional group X of the complex is a reactive group that can be coupled to an immunological active substance or an activatable group that can be converted in a simple manner into such a reactive group. The group X is preferably an activated carboxylic acid group such as a carboxylic acid halogenide, a carboxylic acid anhydride or an active ester e.g. an N-hydroxysuccinimide ester, p-nitrophenyl ester, pentafluorophenyl ester, imidazolyl ester or N-hydroxybenzotriazolyl ester, a maleimide, an amine, a carboxylic acid, a thiol, a halogenide, a hydroxyl or a group which can be photoactivated.

In addition the complex contains one or several negatively charged groups A required for charge equalization. Examples of suitable negatively charged groups are halogenides, $OH^-$, carbonate, alkyl carboxylate e.g. trifluoroacetate, sulfate, hexafluorophosphate and tetrafluoroborate groups. Hexafluorophosphate, trifluoroacetate and tetrafluoroborate groups are particularly preferred.

The metal complex according to the invention differs from the metal complexes known from the state of the art in that it contains at least one hydrophilic group selected from $C_2$–$C_3$ alkyleneoxy units, $C_2$–$C_3$ alkylenethio units, $C_2$–$C_3$ alkyleneamino units and polyhydroxy units.

The polyhydroxy units are preferably selected from groups of formulae (IIa) or (IIb):

$$—NR—W \qquad (IIa)$$

$$—O—W \qquad (IIb)$$

in which W denotes an organic residue with at least two hydroxy groups and R denotes hydrogen or $C_1$–$C_5$ alkyl, preferably hydrogen or $C_1$–$C_3$ alkyl. The organic residue W preferably contains 2 to 6 and particularly preferably 2 to 4 hydroxy groups. Furthermore W should advantageously contain 2 to 10 and in particular 3–6 carbon atoms. Specific examples of suitable polyhydroxy units are residues of polyalcohols such as glycerol or aminopolyalcohols. A preferred aminopolyalcohol is Tris (2-amino-2-(hydroxymethyl)-1,3-propanetriol). In this case the polyhydroxy unit has the formula NH—$C(CH_2OH)_3$. The polyalcohols or aminopoly-alcohols are preferably coupled to the metal complex in the form of esters or amides.

The $C_2$–$C_3$ alkyleneoxy, $C_2$–$C_3$-alkylenethio and $C_2$–$C_3$-alkyleneamino units of the metal complex according to the invention are preferably $C_2$ units and in particular ethyleneoxy units. The complex preferably contains 1 to 30 and particularly preferably 2 to 20 $C_2$–$C_3$ alkyleneoxy, $C_2$–$C_3$ alkylenethio or $C_2$–$C_3$ alkyleneamino units per metal cation. These units are components of substituents of the heterocyclic ligands of the metal complex. They can be present in the linker between one of the ligands and the reactive or activatable functional group X or/and in monosubstituents. The alkyleneoxy, alkylenethio or alkyleneamino units can also be linked together via a bridgehead which can optionally carry a functional group X. On the other hand several complex units can also be linked together via the bridgehead. Examples of preferred embodiments of the metal complexes of the present invention are stated in the following.

In a first embodiment of the present invention the metal complex according to the invention has the general

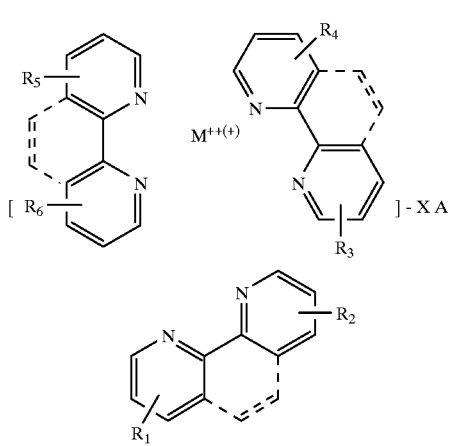

(III)

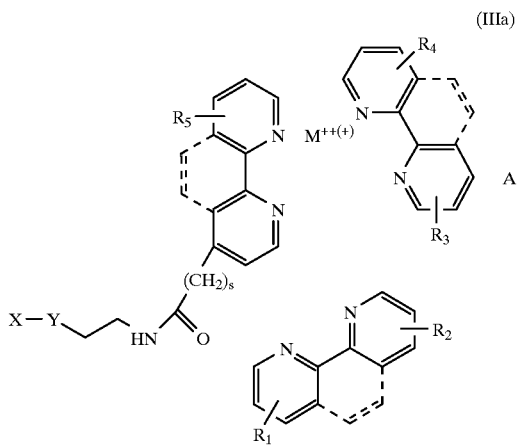

(IIIa)

in which M, X and A are defined as above, $R_1$, $R_2$, $R_3$, $R_4$ and $R_5$ are defined as above, s is an integer from 0 to 6 and preferably from 1 to 4 and Y denotes a hydrophilic linker group with 1 to 10, preferably with 2 to 6 hydrophilic units selected from $C_2$–$C_3$ alkyleneoxy units, $C_2$–$C_3$ alkylenethio units, $C_2$–$C_3$ alkyleneamino units, in particular ethyleneoxy units.

However, the functional group X does not have to be linked to the ligand via a hydrophilic linker. In this case the metal complex according to the invention preferably has the general formula (IIIb):

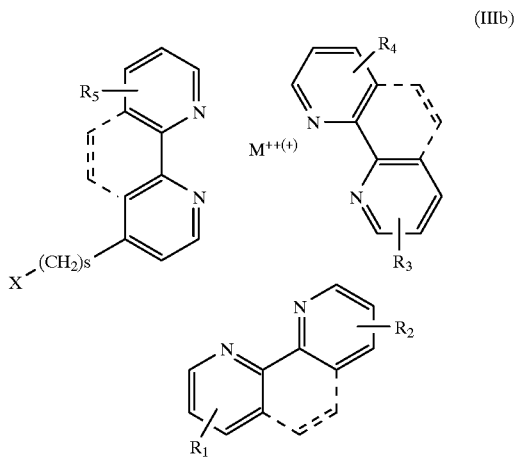

(IIIb)

in which M, X and A are defined as above, $R_1$, $R_2$, $R_3$, $R_4$, $R_5$ and $R_6$ are the same or different and each denotes one or several substituents provided that X is linked to one of the ligands via one of the substituents $R_1$, $R_2$, $R_3$, $R_4$, $R_5$ or $R_6$ and that at least one of the substituents $R_1$, $R_2$, $R_3$, $R_4$, $R_5$ or $R_6$ contains at least one hydrophilic group selected from $C_2$–$C_3$ alkyleneoxy, $C_2$–$C_3$ alkylenethio, $C_2$–$C_3$ alkyleneamino units.

The ligands of the complex may also be substituted phenanthroline or bipyridine systems depending on the presence or absence of the groups indicated by the broken lines.

The substituents $R_1$, $R_2$, $R_3$, $R_4$, $R_5$ and $R_6$ on the ligands are—provided they do not contain a hydrophilic group—preferably hydrogen, $C_1$–$C_5$ alkyl and in particular $C_1$–$C_3$ alkyl. Overall the hydrophilic groups preferably contain 1 to 30 and particularly preferably 2 to 20 alkyleneoxy, alkylenethio or/and alkyleneamino units, especially ethyleneoxy units.

The hydrophilic group can be a component of a linker between the functional group X capable of coupling and one of the ligands. In this case the metal complexes preferably have the general formula (IIIa):

in which M, X and A are defined as above, $R_1$, $R_2$, $R_3$, $R_4$ and $R_5$ are defined as above, provided that $R_1$, $R_2$, $R_3$, $R_4$ or/and $R_5$ contains a hydrophilic substituent group which each comprise 1 to 10, preferably 2 to 6 $C_2$–$C_3$ alkyleneoxy units, $C_2$–$C_3$ alkylenethio units or/and $C_2$–$C_3$ alkyleneamino units, in particular ethyleneoxy units.

Figure 1B:
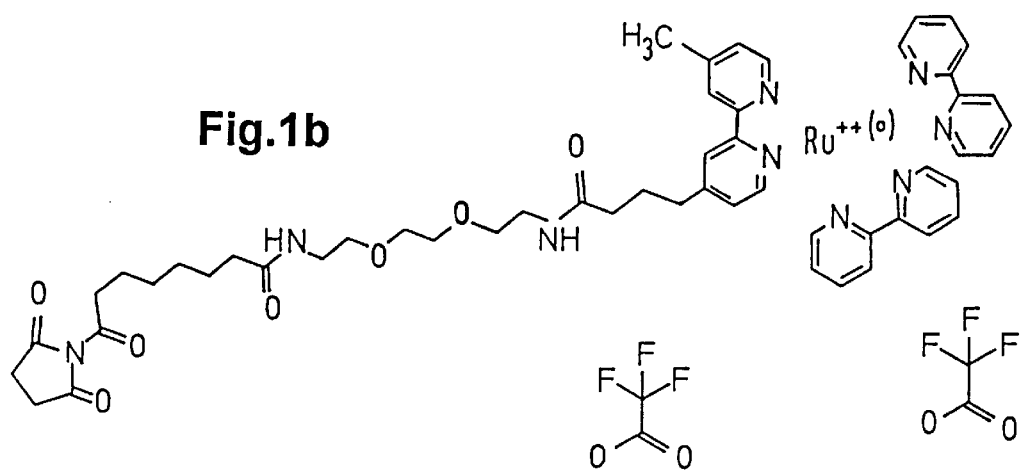

An example of a compounds of formula (IIIa) is shown in FIG. 1a and 1b. These compounds contain the hydrophilicity only in the linker between the group X—a maleimide (FIG 1a) or an N-hydroxysuccinimide ester (FIG. 1b)—and a ligand. The other ligands can however likewise have hydrophilic substituents. An example of a compound of formula (IIIb) is shown in FIG. 1b. In this case the group X is an N-hydroxysuccinimide ester.

The ligands of the metal complex according to the invention can also be linked together so that the metal complex is present in the form of a semicage or cage. A preferred embodiment of a metal complex according to the invention in the form of a semicage or cage has the general formula (IV):

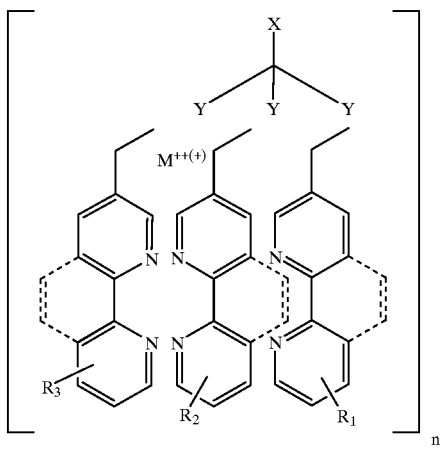

(IV)

in which M, X, n and A are defined as above, $R_1$, $R_2$ and $R_3$ are the same or different and each denote one or several substituents—as defined above—on the bipyridine or phenanthroline ligand and Y in each case denotes a hydrophilic linker group which comprises 1 to 10 hydrophilic units selected from $C_2$–$C_3$ alkyleneoxy, $C_2$–$C_3$ alkylenethio and $C_2$–$C_3$ alkyleneamino units, in particular ethyleneoxy units.

If the substituents $R_1$, $R_2$ and $R_3$ in formula (IV) are covalently linked together optionally via hydrophilic linker groups, then the complex of formula (IV) is in the form of a cage.

Figure 2:
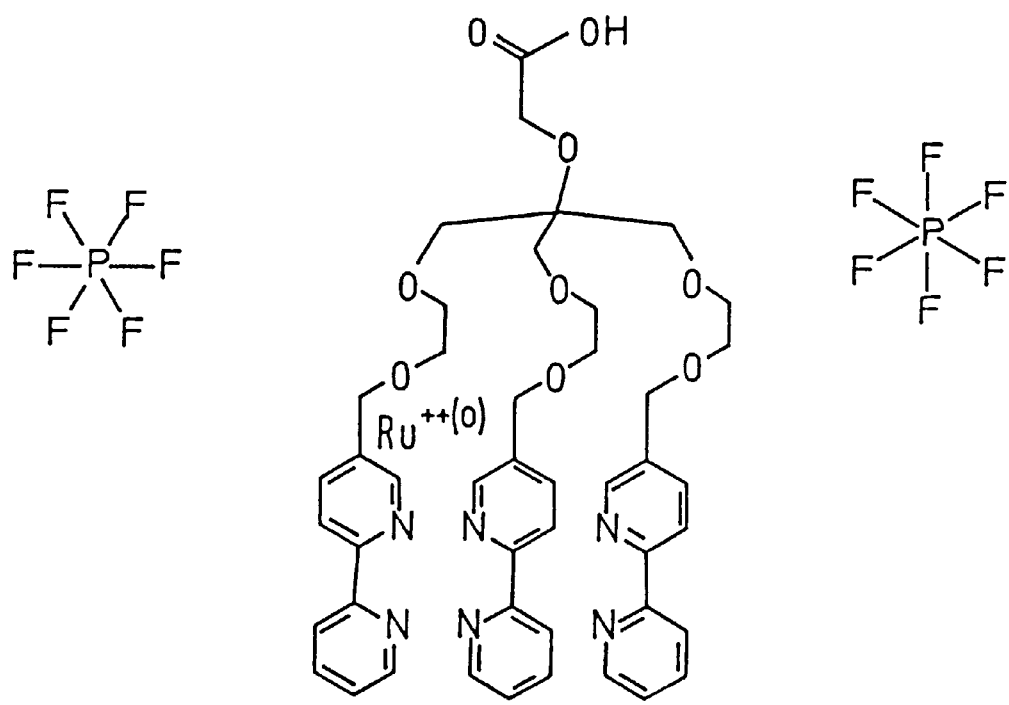
Figure 3A:
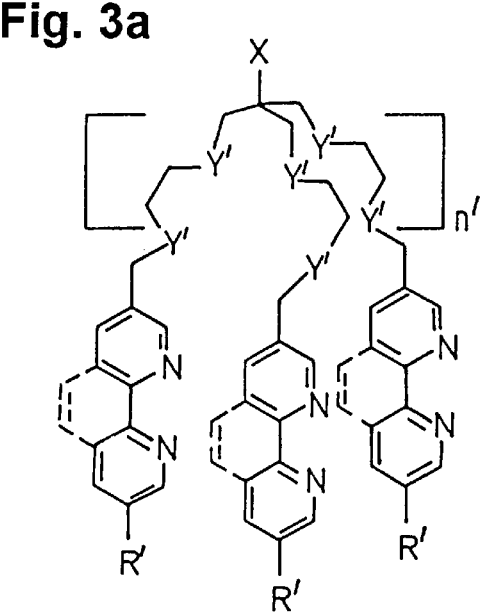
Figure 3B:
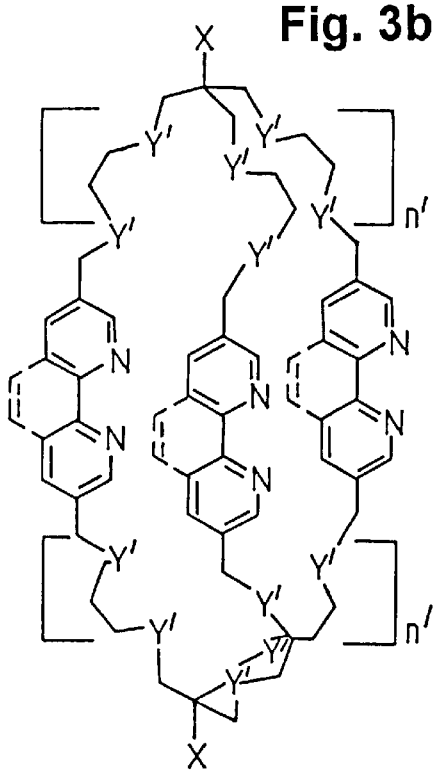

Examples of complexes of formula (IV) in a semicage form are shown in FIGS. 2 and 3a. An example of a complex in a cage form is shown in FIG. 3b. The group X in FIG. 2 is a carboxyl residue. The metal cation and the anions are not shown in FIGS. 3a and 3b.

The complex of formula (IV) may not only be present as a monomer but as an oligomer composed of preferably up to 5 individual metal complexes. In this case the functional group X capable of coupling can for example be a substituent on an aromatic nucleus e.g. a phenyl nucleus in which case two or several of the remaining substituent positions of the aromatic nucleus can be substituted by a metal complex in the form of a semicage or cage.

Figure 4:
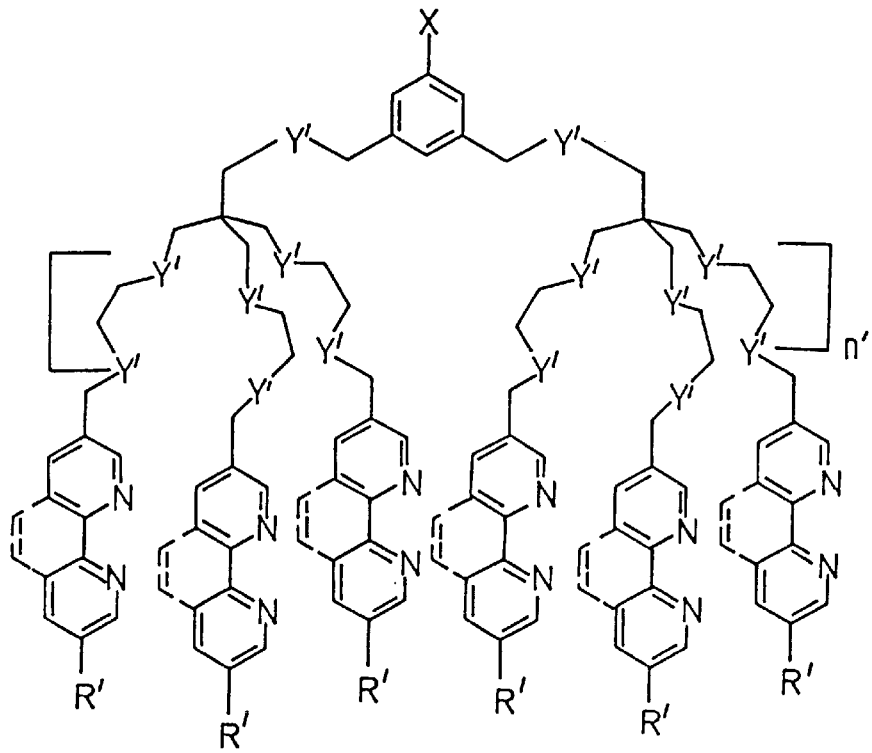
Figure 5:
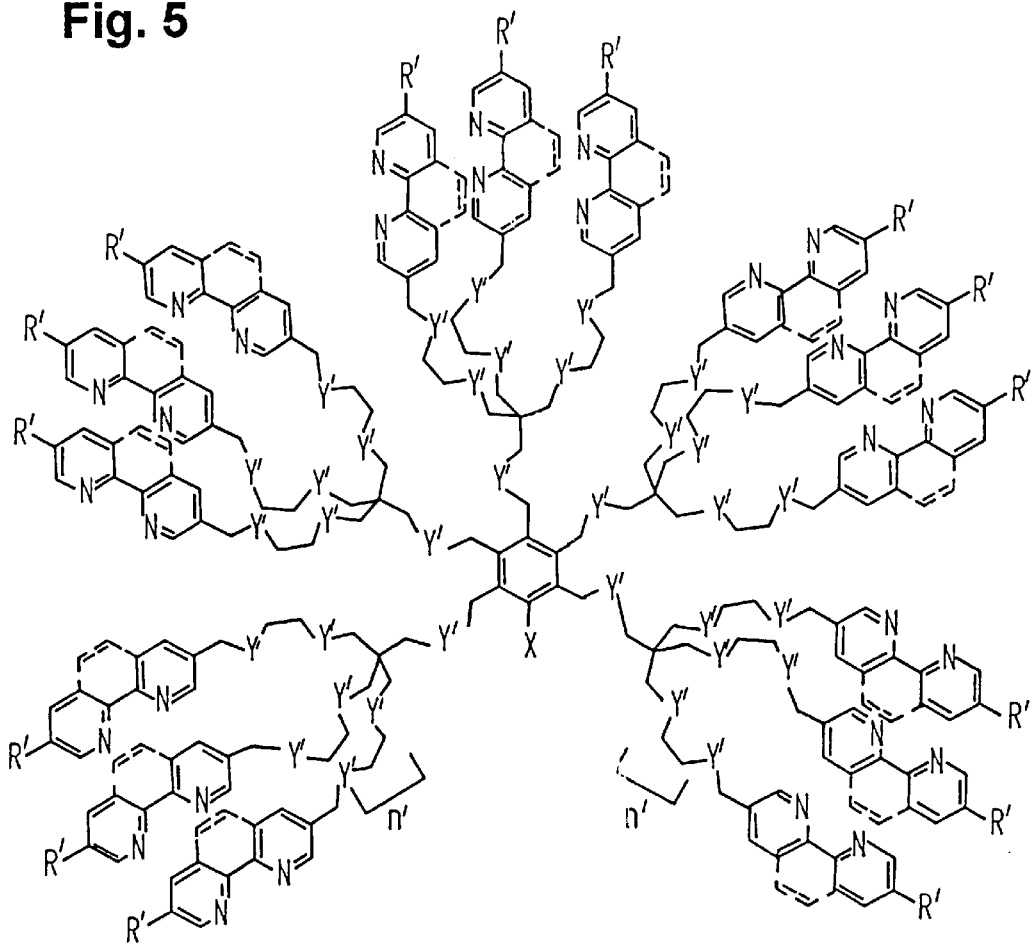

Examples of oligomeric metal complexes of formula (IV) are shown in FIGS. 4 and 5. The metal ions and anions are not shown in these figures.

In a further preferred embodiment of the present invention the metal complex is substituted with polyhydroxy units and has the general formula (V):

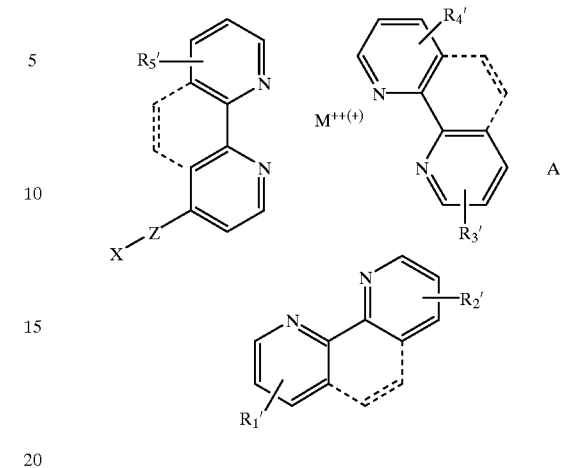

(V)

in which M, X and A are defined as above, Z denotes a linker group, $R'_1$, $R'_2$, $R'_3$, $R'_4$ and $R'_5$ are the same or different and each denotes one or several substituents e.g. hydrogen or $C_1$–$C_5$ alkyl, in particular $C_1$–$C_3$ alkyl and s is an integer from 0 to 6, preferably of 1 to 4 provided that $R'_1$, $R'_2$, $R'_3$ or/and $R'_4$ contain a hydrophilic substituent group which comprises a polyhydroxy unit.

The ligand X of the metal complex (V) can be coupled to the ligand via a hydrophilic linker e.g. a linker according to formula (IIIa) and also via a linker according to formula (IIIb). The substituent $R'_5$ is preferably hydrogen or a $C_1$–$C_5$ alkyl group and in particular a $C_1$–$C_3$ alkyl group.

Figure 6:
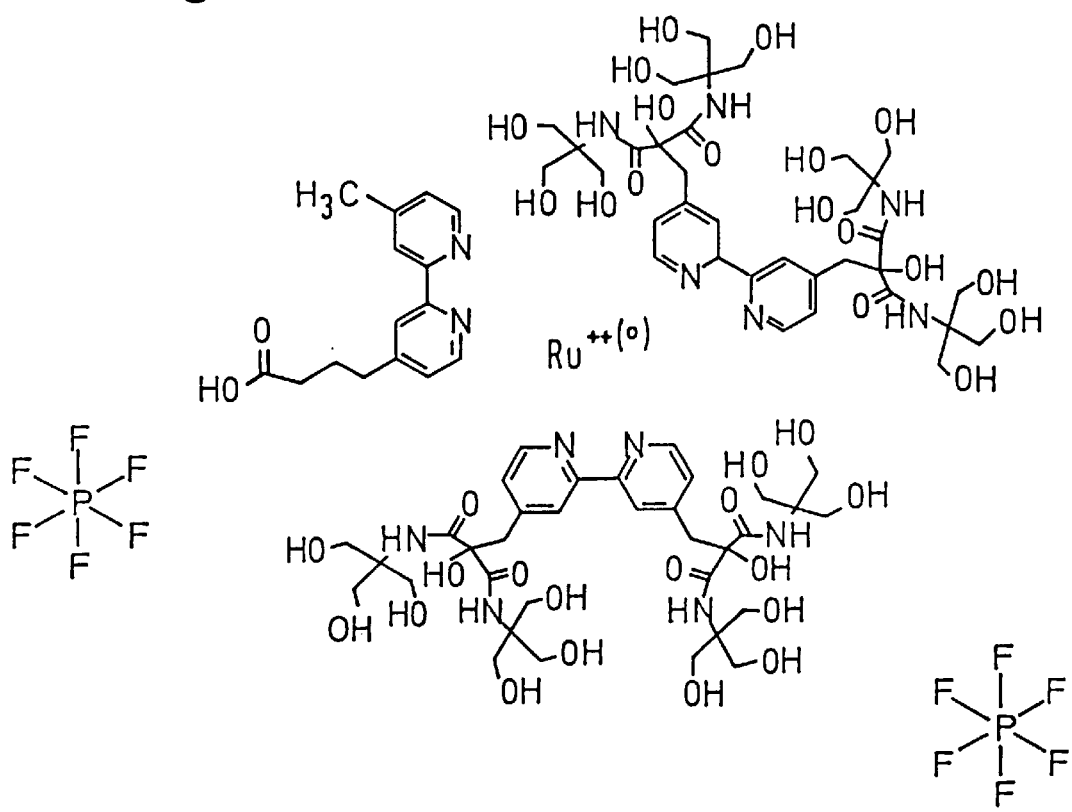

An example of a compound of formula (V) is shown in FIG. 6. The group X is a carboxyl residue.

The OH groups of the polyhydroxy units of metal complexes of the general formula (V) are optionally substituted by hydrophilic groups e.g. by $C_2$–$C_3$ alkylenoxy; $C_2$–$C_3$ alkylenethio units or/and $C_2$–$C_3$ alkyleneamino units.

In a specific embodiment of the present invention the hydrophilic substituent groups of the OH groups of the polyhydroxy units are dendrimers of the general formula (VIa) or (VIb):

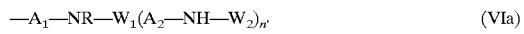

(VIa)

(VIb)

in which $A_1$ and $A_2$ are the same or different and denote linker groups, $W_1$ and $W_2$ are the same or different and denote an organic residue with at least 2 hydroxy groups, R denotes hydrogen or $C_1$–$C_5$ alkyl and preferably hydrogen or $C_1$–$C_3$ alkyl and n' is 0 or corresponds to the number of hydroxy groups of $W_1$.

The linker groups $A_1$ and $A_2$ are preferably groups of formula $(CH_2)_m{'}C(=O)$—, in which m' is 1 to 5 and in particular 1 to 3.

The groups $W_1$ and $W_2$ are preferably polyhydroxy units which are defined as for the groups of formulae (IIa), (IIb). If n' is zero, then a dendrimer of the first generation is present. If n' corresponds to the number of hydroxy groups of $W_1$ a dendrimer of the second generation is present. The hydroxy terminal groups of the dendrimers can be optionally substituted e.g. by a linker group having the formula $A_3$—R' in which $A_3$ is defined like the linker groups $A_1$ and $A_2$ and R' denotes $C_1$–$C_5$ alkyl and preferably $C_1$–$C_3$ alkyl.

The metal complexes according to the invention are produced by reacting a metal salt e.g. a metal halogenide with the appropriate ligands and optionally subsequently replacing the halogenide ion by hexafluorophosphate or tetrafluoroborate anions. Such processes are described in the state of the art e.g. in EP-B-0 178 450 and EP-B-0 255 534. Reference is hereby made to this disclosure.

The production of hydrophilic N-heterocyclic ligands can be carried out in a simple manner by substitution on the aromatic ligand e.g. via a tosylate. The hydrophilic linker that carries the functional group X can also be coupled in a corresponding manner.

The production of metal complexes of formula (IV) with a semicage or cage structure can for example be carried out by attaching alkyleneoxy, alkylenethio or/and alkyleneamino units to the bipyridine or phenanthroline ligands and linking these units to a bridgehead via an ether or an amide bond. If two bridgeheads are used it is possible to obtain cage structures. The linking of three ligands to a trivalent bridgehead e.g. Tris is preferred. The complex itself is produced by reaction with metal salts as described above.

Figure 9A:
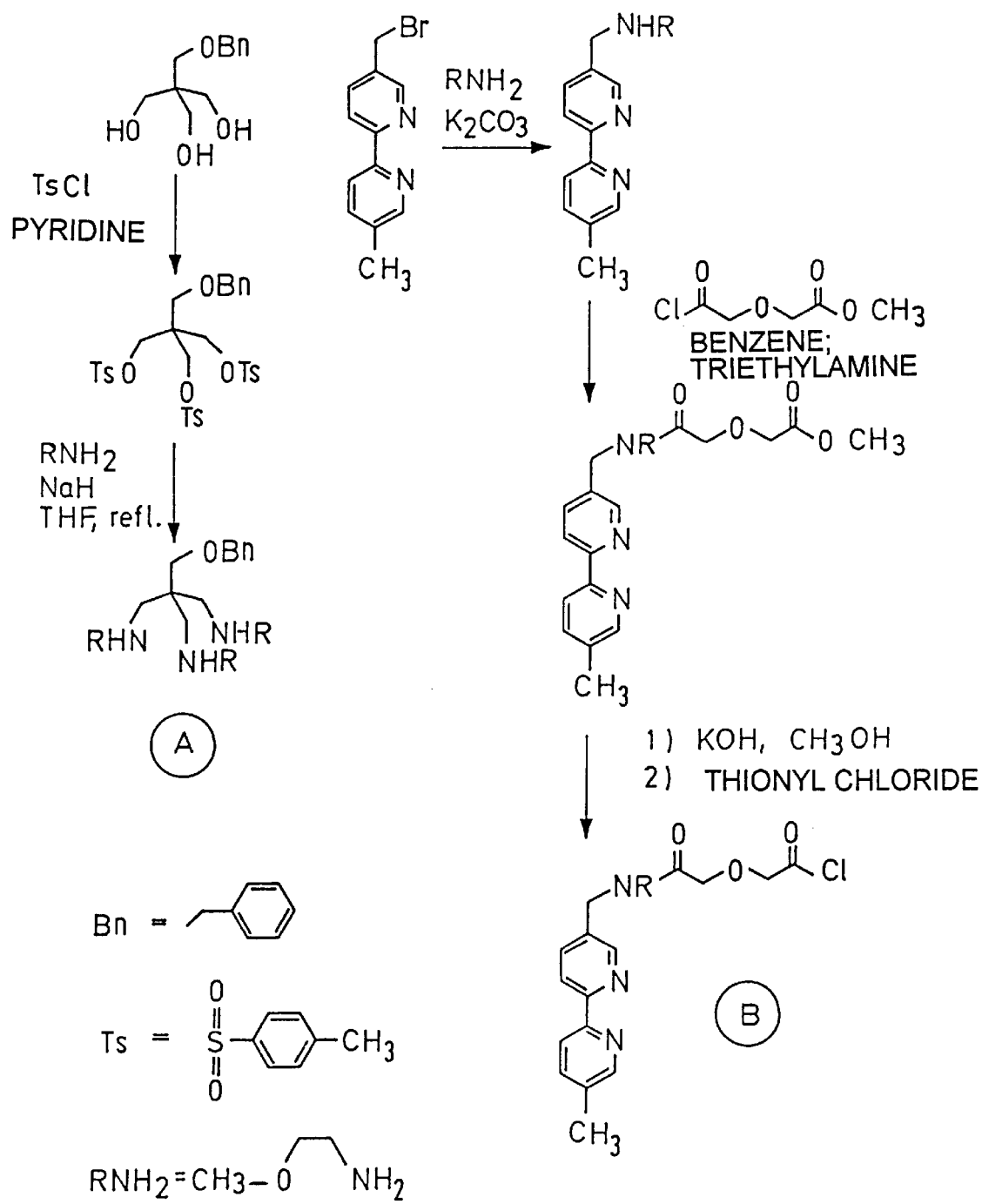
Figure 9B:
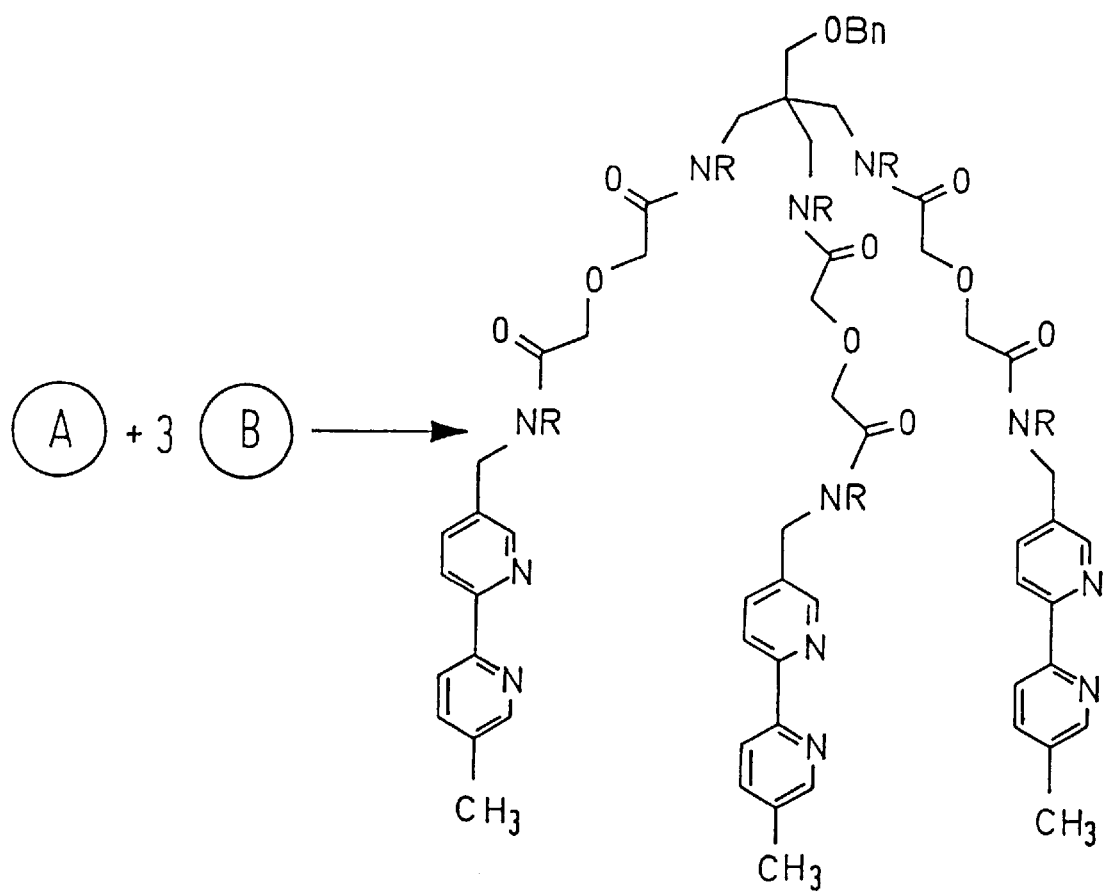

The production of metal complexes in a cage or semicage form can be achieved according to reaction scheme III (FIGS. 9a and 9b).

The metal complexes of the general formula (V) are for example produced by a reaction according to scheme I (FIG. 7) in which an appropriately substituted ligand is reacted with an amino polyalcohol or a partially protected polyalcohol in which hydrophilic groups of formulae (IIa) or (IIb) are attached to the ligand.

Figure 8:
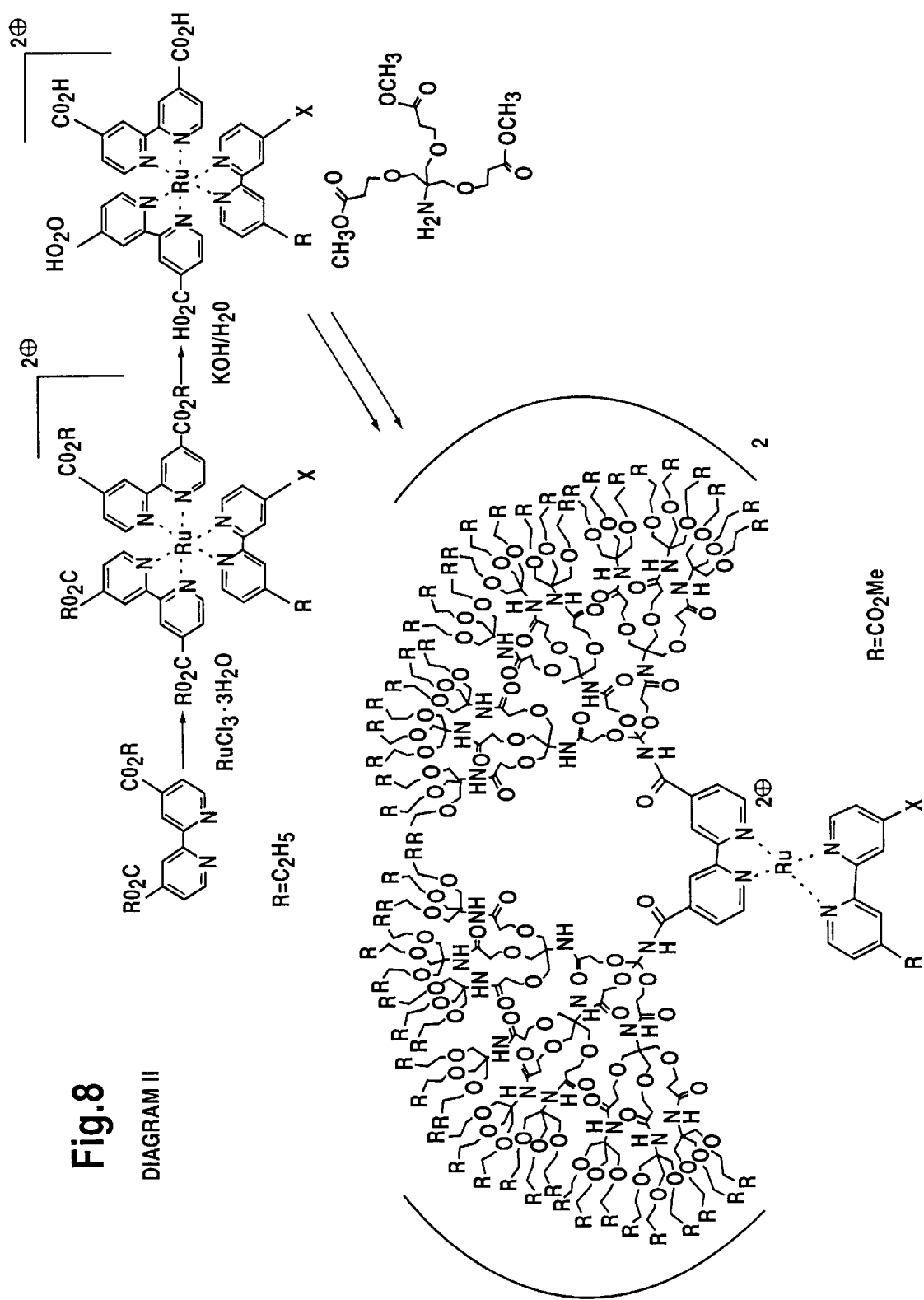

Dendritical metal complexes can be produced according to reaction scheme II (FIG. 8).

A further subject matter of the present invention is a conjugate comprising a biological substance to which at least one metal complex according to the invention is coupled. Examples of suitable biological substances are cells, viruses, subcellular particles, proteins, lipoproteins, glycoproteins, peptides, polypeptides, nucleic acids, oligosaccharides, polysaccharides, lipopolysaccharides, cellular metabolites, haptens, hormones, pharmacologically active substances, alkaloids, steroids, vitamins, amino acids and sugars.

The metal complex is preferably coupled to the biologically active substance via the reactive or activatable functional group of the metal complex which can covalently couple to a functional group of the biological substance. If the functional group is an active ester, it can for example be coupled to the free amino groups of the biological substance. If the functional group is a maleinimide residue, it can be coupled to the free SH groups of the biological substance. Functional groups of the biological substance can also be activated in a similar manner which can subsequently react for example with a free carboxylic acid, amino or thiol group of the metal complex.

In a particularly preferred embodiment of the present invention the metal complexes are coupled to a peptide which preferably has a maximum length of 50 amino acids and particularly preferably of 30 amino acids. The production of these peptides labelled with a metal complex is preferably carried out by synthesizing a peptide with the desired amino acid sequence on a solid phase in which a) after the synthesis an activated metal complex, preferably a metal complex-active ester derivative, is coupled to the N-terminal amino group of the peptide or/and b) during the synthesis an amino acid derivative that is covalently coupled to a metal complex is introduced in at least one position of the peptide. The coupling of the metal complex to the N-terminal amino acid of the peptide is preferably carried out before cleaving the peptide from the solid phase and before cleaving protecting groups on reactive side groups of the amino acid derivatives used for the peptide synthesis.

The peptides preferably contain an immunologically reactive epitope region and a spacer region wherein at least one metal complex marker group is coupled to the spacer region. The spacer region preferably has a length of 1 to 10 amino acids and is located at the amino or/and carboxy terminus of the peptide.

The spacer region preferably contains amino acids which have charges or/and can form hydrogen bridges. The amino acids of the spacer region are preferably formed from the group comprising glycine, β-alanine, γ-aminobutyric acid, ε-aminocaproic acid, lysine and compounds of the structural formula $NH_2-[(CH_2)_yO]_x-CH_2-CH_2-COOH$ in which y is 2 or 3 and x is 1 to 10.

The epitope regions of the peptides are preferably derived from pathogenic organisms e.g. bacteria, viruses and protozoa or from autoimmune antigens. The epitope region is particularly preferably derived from viral antigens e.g. the amino acid sequences of HIVI, HIVII or hepatitis C virus (HCV).

Further preferred examples of biological substances are biotin, nucleic acids, antibodies or antibody fragments, polypeptide antigens i.e. immunologically reactive polypeptides or haptens i.e. organic molecules with a molecular weight of 150 to 2000, in particular molecules with a steroid backbone such as cardenolides, cardenolide-glycosides (e.g. digoxin, digoxigenin), steroid alkaloids, sexual hormones (e.g. progesterone), glucocorticoids etc. Further examples of haptens are prostaglandins, leuco-en-diines, thromboxanes, pharmacologically active substances etc.

Yet a further subject matter of the present invention is the use of the metal complexes according to the invention or of the conjugates according to the invention in an immunological detection method.

In this method the metal complex is used as a marker group with the aid of which it is possible to qualitatively or/and quantitatively determine an analyte in a sample solution. The metal complex is preferably detected by electrochemiluminescence in which case luminescent species are generated electrochemically at the surface of an electrode. Examples for carrying out luminescence assays using metal complexes of the state of the art may be found in EP-A-0 580 979, WO 90/05301, WO 90/11511 and WO 92/14138. Reference is hereby made to the methods and devices for luminescence assays disclosed therein. Electrochemiluminescence assays are carried out in the presence of a solid phase which is preferably composed of microparticles and in particular of magnetic microparticles which are provided with a reactive coating e.g. with streptavidin. In this manner it is possible to detect immune complexes containing a metal complex as a marker group that are bound to a solid phase.

The electrochemiluminescence measurement is preferably carried out in the presence of a reducing agent for the metal complex e.g an amine. Aliphatic amines and in particular primary, secondary and tertiary alkylamines, the alkyl groups of which each have 1 to 3 carbon atoms are preferred. Tripropylamine is particularly preferred. The amine can, however, also be an aromatic amine such as aniline or a heterocyclic amine. The reducing agent can already be integrated into the ligand sphere of the complex. Such systems are especially suitable for the determination of analytes that are present in a highly concentrated form.

In addition a non-ionic surface-active agent may also be present as an amplifier e.g. an ethoxylated phenol. Such substances are for example commercially available under the names Triton X100 or Triton N401.

On the other hand the luminescent metal complex can also be detected by fluorescence in which case the metal chelate is excited by irradiation with light of a suitable wavelength and the resulting fluorescent radiation is measured. Examples for carrying out fluorescence assays may be found in EP-A-0 178 450 and EP-A-0 255 534. Reference is hereby made to this disclosure.

The present invention is further elucidated by the following examples and figures.

Figure 1C:
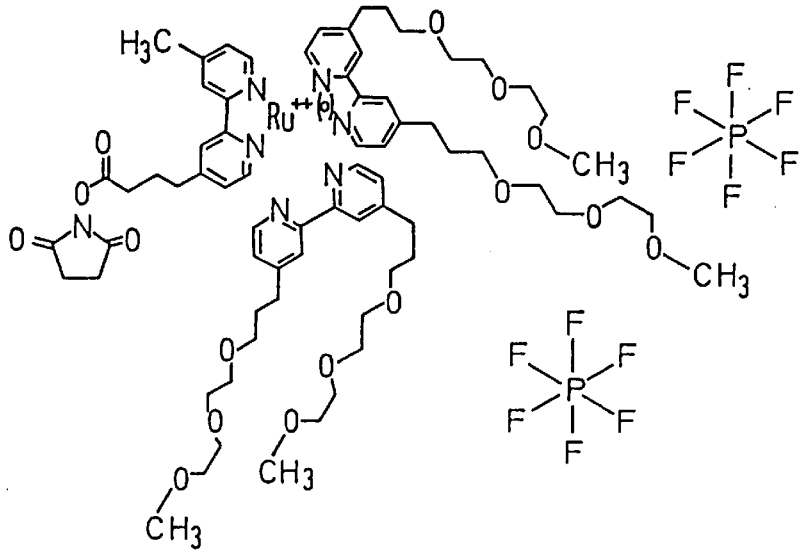
Figure 7:
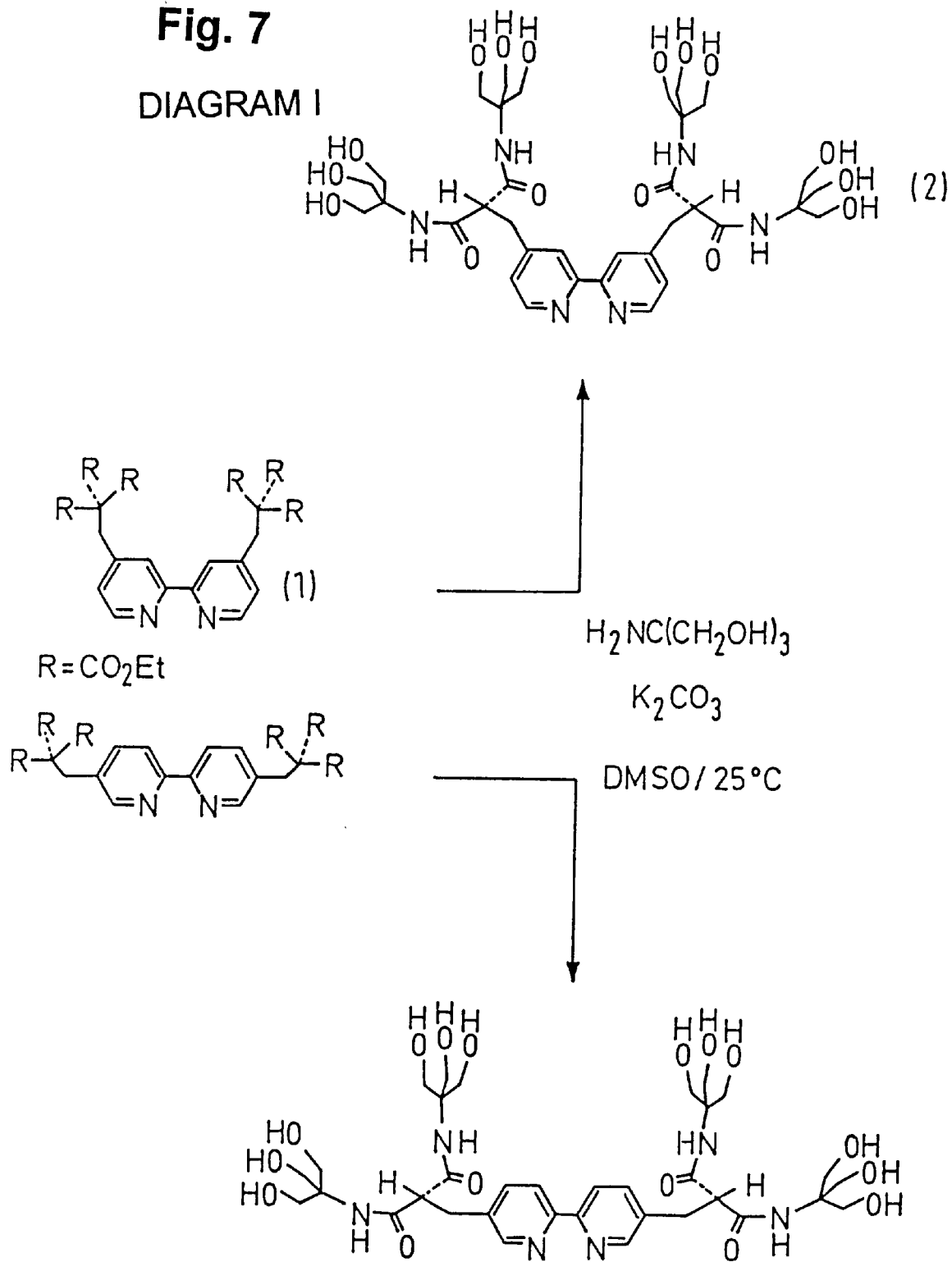
Figure 10:
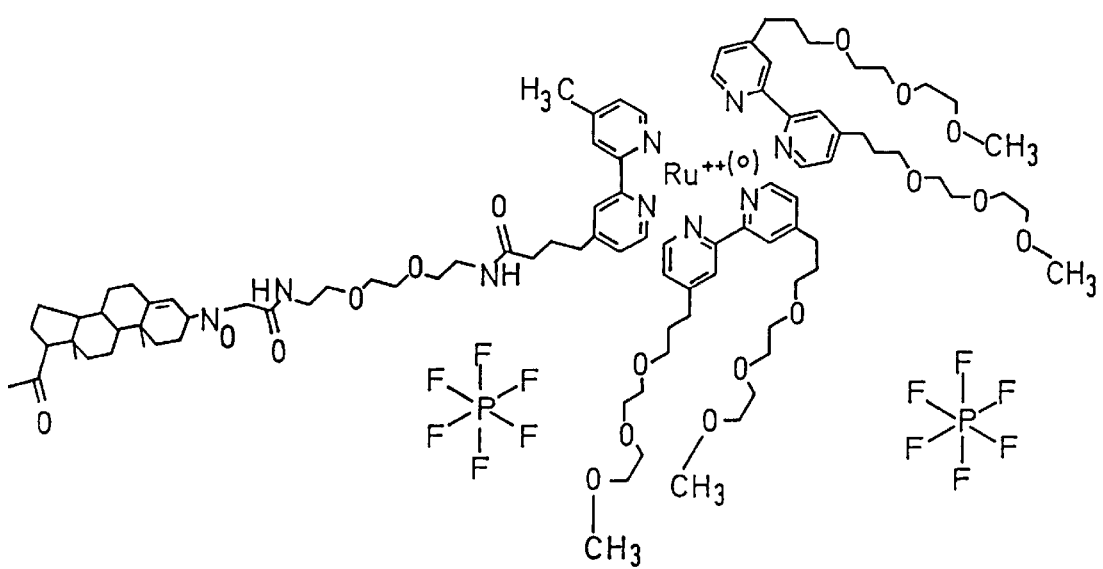

FIG. 1a shows a metal complex of formula (IIIa),
FIG. 1b shows a metal complex of formula (IIIa),
FIG. 1c shows a metal complex of formula (IIIb),
FIG. 2 shows a metal complex of formula (IV),
FIG. 3a shows a metal complex of formula (IV),
FIG. 3b shows a metal complex of formula (IV),
FIG. 4 shows a metal complex of formula (IV),
FIG. 5 shows a metal complex of formula (IV),
FIG. 6 shows a metal complex of formula (V),
FIG. 7 shows a reaction scheme for the production of metal complexes of formula (V),
FIG. 8 shows a further reaction scheme for the production of metal complexes of formula (V),
FIGS. 9a and 9b show a reaction scheme for the production of metal complexes of formula (IV),and
FIG. 10 shows a metal complex-progesterone conjugate.

EXAMPLE 1
Production of a hydrophilic bipyridine ligand (4,4'-bis(methoxy-ethoxy-ethoxy)-bipyridine)

50 ml of a solution of lithium diisopropylamide in a mixture of cyclohexane, ethylbenzene and THF is cooled to −78° C. 350 ml of a solution of 50 mml bipyridine in THF is added dropwise. It is allowed to stir for two hours and a solution of 100 mmol methoxy-ethoxy-ethoxy-tosylate in THF is added dropwise. After 1 hour at −78° C. the reaction mixture is allowed to stand overnight at room temperature. Then an aqueous sodium chloride solution is added. Subsequently the THF is removed using a rotary evaporator and the residue is extracted with ethyl acetate.

The product is purified chromatographically on silica gel. Eluant: ethyl acetate-methanol-ammonia 95/4/1 or amino silica gel using ethyl acetate-petroleum ether as the eluant.

H-NMR(CDCl$_3$): 3.6 ppm (m.CH$_2$CH$_2$)=16H 7.12–8.5 ppm (bpy)=6H

EXAMPLE 2
Production of a bis(bis-ethylene glycol-bipyridine)dichlororuthenium complex Ruthenium trichloride is dissolved with a double-molar excess of the ligand synthesized in example 1 and a 7- to 8-fold excess of lithium chloride in DMF and boiled for 6 hours under reflux. The solvent is removed, the residue is dissolved in water and extracted with ethyl acetate and subsequently with chloroform. The chloroform phases are pooled, dried, filtered and concentrated on a rotary evaporator.

The product is purified by thin layer chromatography on amino silica gel using acetonitrile/H$_2$O 10/1 (Rf=0.58).

EXAMPLE 3
Synthesis of bis(bis-ethylene glycol-bipyridine)-4(4(4'-methyl-2,2'bipyridyl))-butanoic acid 3.0 g of the ruthenium complex synthesized in example 2 was dissolved under argon in 240 ml of an ethanol-water mixture. 0.82 g bipyridyl-butanoic acid derivative is added and heated for three hours under reflux. The solution is concentrated, washed with ethyl acetate and extracted with chloroform. It is rotary evaporated and the residue is purified on SP-Sephadex (eluant: NaCl/HCl in water).

Yield: 500 mg, purity (HPLC): 93%
MS (PosLIMS): 1455.5=Ru$^{2+}$ complex PF$_6^-$

EXAMPLE 4
Synthesis of a hydrophilic metal complex active ester derivative 260 mg of the complex synthesized in example 3 was dissolved in methylene chloride and admixed with an equimolar amount of dicyclohexylcarbodiimide/N-hydroxysuccinimide ester. It is allowed to stir for twelve hours, the DCH is removed by filtration and it is rotary evaporated. The crude product is purified by preparative HPLC. The yield is 85%.

EXAMPLE 5
Synthesis of a hydrophilic metal complex maleimide derivative 150 g of the metal complex Ru(bipyridine)$_2$(bipyridine-CO-N-hydroxysuccinimide ester) according to EP-A-0 580 979 are reacted for ca. 12 hours together with 100 mg maleimido-amino-dioxaoctane (MADOO) and triethylamine in methylene chloride. The reaction mixture is shaken out three times with water and the residue from the organic phase is purified on a Sephadex-LH20 column using methylene chloride/methanol. The compound Ru(bpy)$_2$(bpy-CO-MADOO) shown in FIG. 1a is obtained.

MS: M$^+$=1025.3 (corresponds to Ru$^{2+}$PF$_6^-$ complex).

EXAMPLE 6
Preparation of a hydrophilic metal complex active ester derivative 0.5 mmol of the ruthenium complex used as a starting material in example 5 in 20 ml dichloromethane is reacted with 0.5 mmol mono-Boc-diaminodioxaoctane in 20 ml dichloromethane and one equivalent of triethylamine. The purification is carried out as described in example 5. The Boc protecting group is cleaved according to standard methods (trifluoroacetic acid/methylene chloride).

The resulting product is reacted for 2 h at room temperature with an equimolar amount of suberic acid-bis-N-hydroxysuccinimide ester in dimethylformamide. The solvent is removed, the residue is taken up in water and lyophilized. The resulting product is shown in FIG. 1b.

H-NMR: 7.2–8.9 ppm: bipyridine (22H); 2.8 ppm NHS ester (4H).

EXAMPLE 7
Preparation of a metal-complex-hapten conjugate 10 mg of the N-hydroxysuccinimide ester from example 4 is dissolved together with 3.2 mg progesterone-3-carboxymethyl-oxime-diamondioxyoctane in 2 ml methylene chloride, 1.2 µl triethylamine is added and it is stirred for 12 hours at room temperature. The solvent is removed and the residue is purified on Sephadex. The resulting conjugate is shown in FIG. 10.

MS (posLIMS): M+=1923.0 (ruthenium-complex-progesterone conjugate$^{2+}$ trifluoroacetate)

EXAMPLE 8
Production of metal chelate labelled peptides

The metal chelate labelled peptides were produced by means of fluorenylmethyloxycarbonyl-(Fmoc)-solid phase peptide synthesis on a batch peptide synthesizer e.g. from Applied Biosystems A431 or A433. For this 4.0 equivalents of the amino acid derivatives shown in Table 1 were used in each case.

TABLE 1

| | |
|---|---|
| A | Fmoc—Ala—OH |
| C | Fmoc—Cys(Trt)—OH |
| D | Fmoc—Asp(OtBu)—OH |
| E | Fmoc—Glu(OtBu)—OH |
| F | Fmoc—Phe—OH |
| G | Fmoc—Gly—OH |
| H | Fmoc—His(Trt)—OH |
| I | Fmoc—Ile—OH |
| K1 | Fmoc—Lys(Boc)—OH |
| K2 | Boc—Lys(Fmoc)—OH |
| K3 | Fmoc—Lys(BPRu)—OH |
| L | Fmoc—Leu—OH |
| M | Fmoc—Met—OH |
| N | Fmoc—Asn(Trt)—OH |
| P | Fmoc—Pro—OH |
| Q | Fmoc—Gln(Trt)—OH |
| R | Fmoc—Arg(Pmc)—OH |
| S | Fmoc—Ser(tBu)—OH |
| T | Fmoc—Thr(tBu)—OH |
| U | Fmoc—βalanine—OH |
| V | Fmoc—Val—OH |
| W | Fmoc—Trp—OH |
| Y | Fmoc—Tyr(tBu)—OH |
| Z | Fmoc—ε-alminocaproic acid—OH |
| Nle | Fmoc—ε-norleucine—OH |
| Abu | Fmoc—γ-alminobutyric acid—OH |

In the variant (a)—introduction of the metal complex after completion of the solid phase synthesis—an activated hydrophilic ruthenium(bipyridyl)$_3$ complex (BPRu) was coupled to the N-terminal amino acid of the peptide. The lysine derivative K1 was used for the spacer region and the lysine derivative K2 was used for the epitope regions According to variant (b) metal chelate groups were introduced into the peptide sequence by direct incorporation of metal chelate-coupled amino acid derivatives e.g. within the sequence via a lysine residue ε-derivatized with a metal chelate active ester e.g. the lysine derivative K3 or N-terminally using an α-derivatized amino acid residue.

The amino acids or amino acid derivatives were dissolved in N-methylpyrrolidone. The peptide was synthesized on 400–500 mg 4-(2',4'-dimethoxyphenyl-Fmoc-aminomethyl) phenoxy resin (Tetrahedron Letters 28 (1987), 2107) loaded with 0.4–0.7 mmol/g (JACS 95 (1973), 1328). The coupling reactions were carried out for 20 min. with 4 equivalents dicyclohexylcarbodiimide and 4 equivalents N-hydroxybenzotriazole with respect to the Fmoc-amino acid derivative in dimethylformamide as the reaction medium. The Fmoc group was cleaved within 20 min. after each synthesis step using 20% piperidine in dimethylformamide.

When cysteine residues were present in the peptide sequence, the solid phase was oxidized immediately after completing the synthesis using iodine in hexafluoroisopropanol/dichloromethane.

The peptide was released from the support and the acid-labile protecting groups were cleaved using 20 ml trifluoroacetic acid, 0.5 ml ethanedithiol, 1 ml thioanisole, 1.5 g phenol and 1 ml water in 40 min. at room temperature. The reaction solution was subsequently admixed with 300 ml cooled diisopropyl ether and kept at 0° C. for 40 min. until complete precipitation of the peptide. The precipitate was filtered, rewashed with diisopropyl ether, dissolved in a small amount of 50% acetic acid and lyophilized. The crude material obtained was purified by means of preparative HPLC on Delta-PAK RP C18 material (column 50×300 mm, 100 Å, 15 μ) over a corresponding gradient (eluant A: water, 0.1% trifluoroacetic acid, eluant: B acetonitrile, 0.1% trifluoroacetic acid) in ca. 120 min. The identity of the eluted material was checked by means of ion spray mass spectrometry.

The metal chelate label was introduced on the free N-terminal amino group of the support-bound peptide according to variant (a) via appropriate active ester derivatives. For this 4 equivalents of a hydrophilic ruthenium (bipyridyl)$_3$ complex (BPRu) per free primary amino function were activated with N-hydroxybenzotriazole/dicyclohexylcarbodiimide, dissolved in a small amount of DMSO, added dropwise and stirred at room temperature. The reaction was monitored by means of analytical HPLC. After cleaving from the support, the product was purified by preparative HPLC. The identity of the eluted material was checked by means of ion spray mass spectrometry.

The peptides were synthesized by a combination of variants (a) and (b) i.e. incorporation of metal-chelate-coupled amino acid derivatives within the sequence, cleaving the N-terminal Fmoc group and reacting the free N-terminal amino group with a metal-chelate active ester derivative.

When the metal chelate-coupled amino acid derivatives were exclusively incorporated directly during the solid phase synthesis according to variant (b), it was no longer necessary to subsequently introduce metal chelate active esters.

The peptide-metal-complex conjugates shown in Table 2 were prepared from the regions gp120, gp41 and gp32 of HIV I and HIV II.

TABLE 2

Ruthenylated linear peptides

| | | |
|---|---|---|
| gp120 | SEQ ID NO:1 | BPRu-UZU-NNTRKSISIGPGRAFYT |
| | SEQ ID NO:2 | BPRU-UZ-NTTRSISIGPGRAFY |
| | SEQ ID NO:2 | BPRu-UZ-NTTRSISIGPGRAFY |
| | SEQ ID NO:1 | NNTRKSISIGPGRAFYT-K(BPRu) |
| | SEQ ID NO:3 | BPRU-UZU-IDIQEERRMRIGPGMAWYS |
| gp41/1 | SEQ ID NO:4 | BPRu-UZU-AVERYLKDQQLLGIW |
| | SEQ ID NO:5 | BPRu-UGGG-QARILAVERYLKDQQLLGIWGASG |
| | SEQ ID NO:5 | BPRu-GGGG-QARILAVERYLKDQQLLGIWGASG |
| | SEQ ID NO:6 | BPRu-UZU-WGIRQLRARLLALETLLQN |
| gp41/2 | SEQ ID NO:7 | BPRu-UZU-LGIWGCSGKLICTTAV |
| | SEQ ID NO:8 | BPRu-UGGG-GCSGKLICTTAVPWNASWS |

TABLE 2-continued

Ruthenylated linear peptides

|  | SEQ ID NO:8 | (GCSGKLICTTAVPWNASWS)K-(BPRu) |
|---|---|---|
| gp41/3 | SEQ ID NO:9 | BPRu-UZU-KDQQLLGIWGSSGKL |
| gp41/4 | SEQ ID NO:10 | BPRu-UZU-ALETLLQNQLLSLW |
| gp32 | SEQ ID NO:11 | BPRu-UZU-NSWGCAFRQVCHTT |
|  | SEQ ID NO:12 | BPRu-GGG-QAQLNSWGCAFRQVCHTTVPWPNDSLT |

The peptides shown in the following Table 3 were synthesized from the NS5 region, the NS4 region and the Core region of HCV.

TABLE 3

Ruthenylated linear peptide

| Core1 | SEQ ID NO:13 | BPRU-GGGG-KNKRNTNRR |
|---|---|---|
| Core1+2 | SEQ ID NO:14 | BPRu-UZU-KNKRNTNRRPQDVKFPGGGQIVGGV |
| NS4/1+2 | SEQ ID NO:15 | BPRu-UZ-SQHLPYIEQG-NleNle-LAEQFKQQALGLLQT |
| NS4/3m | SEQ ID NO:16 | BPRu-UZ-SRGNHVSPTHYVPESDAA |
| NS5/1 | SEQ ID NO:17 | BPRu-UZ-SRRFAQALPVWARPD |
| Core1+2+3 | SEQ ID NO:18 | BPRu-UZ-KNKRNTNRRPQDVKFPGGGQIVGGVLLPRR |
| Core1m | SEQ ID NO:19 | BPRu-UZ-NPKPQKKNKRNTNRR |
| Core3m | SEQ ID NO:20 | BPRu-UZ-GQIVGGVYLLPRRGPRLG |
| Core2m | SEQ ID NO:21 | BPRu-UZ-PQDVKFPGGGQIVGGV |
| NS4/3m-I | SEQ ID NO:22 | BPRu-UZU-SRGNHVSPTHYVPESDAA |
| NS4/1 | SEQ ID NO:23 | BPRu-UZU-SQHLPYIEQ |

Biotin-labelled peptides were either synthesized N-terminally by derivatization on a resin (biotin active ester) or in the sequence using a biotin-active ester ε-derivatized lysine residue (Fmoc-Lys (biotin) —OH).

EXAMPLE 9

Preparation of diethyl-α,α,α',α'-tetrakis (ethoxycarbonyl)-2,2'-bipyridine-4,4'-diyl-dipropionate (corresponding to compound (1) in FIG. 7)

2.00 g (5.8 mmol) 4,4'-bis(bromomethyl)-2,2'bipyridine in 40 ml toluene/DMF (3/2) is added dropwise at 50° C. to a mixture of 6.85 g (29.5 mmol) triethyl-methane-tricarboxylate and 4.1 g (29.7 mmol) potassium carbonate in 50 ml toluene/DMF (3/2) while stirring thoroughly. It is stirred for a further 4 days at 65° C., it is filtered and subsequently the solvent is removed in a vacuum. The oily residue is taken up in 100 ml toluene and successively shaken out three times with water, three times with 7% sodium hydroxide solution and three times with water. The organic phase is pooled and dried over sodium sulfate. After removing the volatile components in a vacuum, the residue is recrystallized from cyclohexane. In order to completely remove impurities it is separated by column chromatography ($SiO_2$, $CHCl_3$/MeOH (10:1) first band).

Colourless crystals (cyclohexane)
Yield: 2.95 g (79%)
Melting point: 116° C.
$^1$H-NMR (250 MHz, $CDCl_3$, 25° C.): δ=1.21 (t, 18H, $^3J$=7.2 Hz), 3.57 (s, 4H), 4.22 (q, 12H, $^3J$=7.2 Hz), 7.25 (dd, 2H, $^3J$=5.1 Hz, $^4J$=1.2 Hz), 8.29 (d, 2H, $^4J$=1.2 Hz), 8.51 (dd, 2H, $^3J$=5.1 Hz, $^4J$=1.2 Hz)
$^{13}$C-NMR (75 MHz, $CDCl_3$, 25° C.): δ=13.96 ($CH_3$), 38.1 ($CH_2$), 62.6 ($H_2CO$), 66.5 (CCO), 123.4, 123.6, 145.9, 149.0, 155 (pyridine-C, CH), 166.5 (C=O).
IR (KBr/solid) [$cm^{-1}$]: 556, 610, 863, 1026, 1186, 1258, 1305, 1594, 1737 vs. 2988
MS-50: (180° C., 70 eV, 300 μA, m/e): found: 644,2585 $C_{32}H_{40}N_2O_{12}$ (644,682)

EXAMPLE 10

Preparation of N,N'-bis(2-hydroxy-1,1-bis(hydroxymethyl)-ethyl)-ethyl-α,α,-bishydroxy-2,2'-bipyridine-4,4'-diyldipropionamide (corresponding to compound (2) in FIG. 7)

967.5 mg (7.00 mmol) potassium carbonate is added while stirring to a solution of 752.7 mg (1.17 mmol) of the hexaester (1) of example 7 and 848.6 mg (7.00 mmol) α,α,α-tris-(hydroxy-methyl)-methylamine in 10 ml DMSO dried over $CaH_2$. After addition of the base the mixture becomes slightly yellow. After stirring for a further 10 minutes at 25° C. the suspension is centrifuged and the solution is decanted from the solid potassium carbonate. The solvent is removed in a vacuum (0.001 mbar) at 30° C. The yellow, oily residue is suspended in a small amount of water and the product is precipitated by the slow addition of dry acetone (distilled over $P_4O_{10}$). It is completely precipitated in the cold. The solution is decanted and the residue is dried for several days over $P_4O_{10}$. A hygroscopic colourless solid remains which is used without further purification.

Yield: 0.652 g (67%)
$^1$H-NMR (250 MHz, DMSO-$d_6$, 25° C.): δ=3.08 (d, 4H), 3.22 (s, 8H), 3.47 (d, 8H, $^2J$=10.8 Hz), 3.55 (d, 8H, $^2J$=11.1 Hz), 3.69 (t, 2H), 4.6–5.1 (bs, OH), 7.27 (d, 2H, pyridyl-H, $^3J$=4.8 Hz), 7.4–7.7 (s, NH), 8.23 (s, 2H, pyridyl-H), 8.51 (d, 2H, pyridyl-H, $^3J$=4.8 Hz)

$^{13}$C-NMR (75 MHz, DMSO-d$_6$, 25° C.): δ=30.7 (CH$_2$), 59.7 (CH$_2$OH), 61.7 (CR$_4$), 63.34 (CR$_4$), 78.5 (CCO), 122.8, 126.0, 146.0, 148.7, 155.0 (pyridine-C, CH$_2$), 170.2 (CONH)

IR (KBr/solid) [cm$^{-1}$]: 3336, 2936, 2880, 1675, 1597, 1559, 1533, 1465, 1363, 1051 (vs)

FAB$^⊕$MS (m-NBA, m/e): 833.3, 855.3, 871.3, 965.2 (M+H)$^⊕$, (M+Na)$^⊕$, (M+K)$^⊕$, (M+Cs)$^⊕$

C$_{34}$H$_{52}$N$_6$O$_{18}$ (832.3)

EXAMPLE 11
Preparation of semicage or cage-like hydrophilic ligands according to reaction scheme III (FIGS. 9a and b)

A:

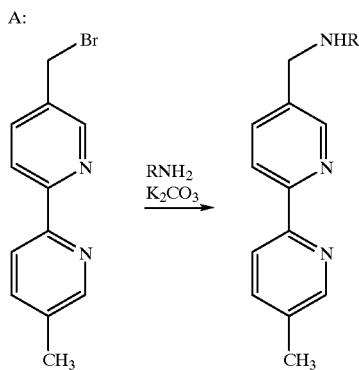

Preparation: 2.6 g (10 mmol) bipyridine-methylbromide 80 ml 2-methoxyethylamine 10 g potassium carbonate Procedure:

The bromide was added to a suspension of powderized potassium carbonate in 2-methoxyethylamine while stirring. The suspension was then stirred for 12 h at room temperature. Subsequently it was filtered, the excess 2-methoxyethylamine was removed by distillation and the residue was dried in a vacuum. The residue was chromatographed (SiO$_2$; CH$_2$Cl$_2$/CH$_3$OH/NH$_3$, 100:10:1).

A light yellow oil was obtained.

Yield: 1.06 g (3.85 mmol) 38%

$^1$H-NMR (250 MHz, CDCl$_3$): 1.95 (s, 1H, NH); 2.26 (s, 3H, pyridyl-CH$_3$), 2.7 (t, $^3$J=5.28 Hz, 2H, OCH$_2$); 3.24 (s, 3H, OCH$_3$); 3.41 (t, $^3$J=5.28 Hz, 2H, NCH$_2$); 3.76 (s, 2H, pyridyl-CH$_2$), 7.5 (dd, $^3$J=8.35 Hz, $^4$J=2.17 Hz, 1H, pyridyl H); 7.69 (dd, $^3$J=8.19 Hz, $^4$J=2.24 Hz, 1H), pyridyl H); 8.17 (d, 3J=8.02 Hz, 1H, pyridyl-H); 8.22 (d, $^3$J=8.24 Hz, 1H, pyridyl-H); 8.39 (d $^4$J=1.84 Hz, 1H, pyridyl H); 8.85 (d, $^4$J=1.85 Hz, 1H, pyridyl H) ppm.

B:

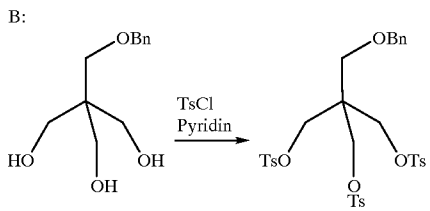

Preparation: 2.26 (10 mmol) tri-alcohol 6.67 (35 mmol) tosyl chloride

Procedure

A solution of the tri-alcohol in 20 ml pyridine was slowly admixed under a protecting gas with a solution of tosyl chloride in 20 ml pyridine while cooling and stirring so that the temperature of the reaction mixture did not exceed 10° C. Then it was stirred for a further 24 h at room temperature. Subsequently it was carefully poured onto a mixture of 10 ml water, 20 ml methanol and 8 ml concentrated hydrochloric acid. The precipitated product and separated oil was filtered or separated and purified chromatographically (SiO$_2$; CH$_2$Cl$_2$/CH$_3$OH/NH$_3$, 100:10:1). One obtains colourless crystals.

Melting point: 57–59° C.

$^1$H-NMR (250 MHz, CD$_2$Cl$_2$): 2.4 (s, 9H, Ar—CH$_3$); 3.25 (s, 2H, CH$_2$); 3.88 (s, 6H, CH$_2$); 4.22 (s, 2H, CH$_2$); 7.02–7.1 (m, 2H, Ar—H); 7.25–7.3 (m, 3H, Ar—H); 7.31 (d, $^3$J=6.46 Hz, 6H, Ar—H); 7.31 (d, $^3$J=6.46 Hz, 6H, Ar—H); 7.67 (d, $^3$J=6.46 Hz, Ar—H) ppm $^{13}$C-NMR and DEPT-135 (62.8 MHz, CDCl$_3$); 145.36; 137.20; 131.75; 43.82 (C$_q$); 130.05; 128.39; 128.33; 127.92; 127.75; 127.23 (CH); 73.28, 66.71; 66.31 (CH$_2$); 21.67 (CH$_3$) ppm

EXAMPLE 13
Use of hydrophilic metal complexes with a charged linker in immunological tests A double-antigen bridge test was carried out to detect specific antibodies against hepatitis C virus (HCV). For this the sample liquid was incubated with a ruthenium-labelled antigen and a biotinylated antigen against the antibody to be determined in the presence of a solid phase coated with streptavidin. The presence of anti-HCV antibodies in the sample liquid was determined by determining the label in the solid phase by electro-chemiluminescence according to the Flash system.

A HCV polypeptide was used as an antigen which contains the amino acids 1207–1488 of HCV. The amino acid sequence and the synthesis of such a polypeptide is described in DE-A-44 28 705.4.

In order to derivatize the HCV polypeptide with ruthenium complexes activated with succinimide ester, the lyophilized polypeptide was dissolved in a 100 mM sodium phosphate buffer pH 6.5, 0.1% SDS at a protein concentration of 10 mg/ml. The pH value was set to 8.5 by addition of 5 M and the solution was supplemented with dithiothreitol to a final concentration of 2 mM. The amount of a ruthenium complex activated with a succinimide ester in DMSO that corresponds to the desired offered stoichiometry was added to this solution and it was subsequently incubated for 60 min at 65° C. while stirring. The reaction was terminated by supplementing the reaction mixture with lysine to a final concentration of 10 mM and incubating it for a further 30 min. Subsequently the mixture was dialysed against 100 mM sodium phosphate buffer pH 6.5, 0.1% SDS. The resulting protein solution was admixed with sucrose (final concentration 6.5% (w/v)) and lyophilized in portions.

For the production of a HCV polypeptide derivatized with a ruthenium complex activated with maleinimide, the polypeptide was taken up in 100 mM sodium phosphate buffer pH 6.5, 0.1% SDS (protein concentration 10 mg/ml). An amount of the maleinimide-activated ruthenium complex in DMSO that corresponds to the desired offered stoichiometry was added to this solution and it was incubated for 60 min at 25° C. while stirring. The reaction was terminated by supplementing the reaction mixture with cysteine to a final concentration of 10 mM and further incubating it for 30 min. Afterwards the reaction mixture was dialysed as described above, admixed with sucrose and lyophilized in portions.

Three experiments were carried out in which different ruthenylated antigens were used each time. For experiment A (comparison) the ruthenium complex according to EP-A-0

580 979 used as the starting material in examples 5 and 6 was coupled in a stoichiometric ratio of 1:3 to the polypeptide. For experiment B the polypeptide was coupled to the hydrophilic ruthenium complex according to the invention produced in example 5 in a stoichiometric ratio of 1:3. For experiment C the polypeptide was coupled to the hydrophilic ruthenium complex produced in example 6 in a stoichiometric ratio of 1:1. In all 3 experiments a polypeptide was used as the biotinylated antigen which had been coupled to a maleimide-activated biotin in a stoichiometric ratio of 1:6. The ruthenylated and biotinylated antigens were in each case used at a concentration of 400 ng/ml test liquid.

The results of experiments A, B and C are shown in Table 2 in ECL counts. It can be seen that a reliable differentiation between a negative serum sample and a critical positive serum sample can only be achieved by using the hydrophilic metal complexes according to the invention as marker groups. This is shown by a higher positive/negative ratio.

TABLE 4

| Experiment | A (comparison) | B | C |
| --- | --- | --- | --- |
| negative sample | 323317 | 84584 | 44274 |
| positive sample | 465769 | 346734 | 313185 |
| Ratio positive/negative | 1.4 | 4 | 7 |

We claim:

1. A metal complex having the formula:

$$[M(L_1L_2L_3)]_n\text{—}X_mA$$

wherein

M is a divalent or trivalent metal cation selected from the group consisting of a rare earth metal cation and a transition metal cation;

$L_1$, $L_2$ and $L_3$ are the same or different, and each is a ligand having at least two nitrogen-containing heterocyclic rings, wherein $L_1$, $L_2$ and $L_3$ are bound to the metal cation via nitrogen atoms;

X is a reactive or activatable functional group selected from the group consisting of an activated carboxylic acid group, a maleimide, a carboxylic acid, a thiol, a halide and a photoactivatable group;

n is 1 to 10;

m is 1 to 6; and

A is at least one negatively charged group, wherein the metal complex contains at least one hydrophilic group selected from the group consisting of a $C_2$–$C_3$ alkyleneoxy group, a $C_2$–$C_3$ alkylenethio group, a $C_2$–$C_3$ alkyleneamino group and a polyhydroxy group, wherein the at least one hydrophilic group is located at at least one of the following locations (a) and (b):

(a) as a substituent or component of a substituent of one of the ligands $L_1$, $L_2$ and $L_3$; and (b) as a linker or component of a linker which links the group X and one of the ligands $L_1$, $L_2$ and $L_3$.

2. The metal complex as claimed in claim 1, wherein M is selected from the group consisting of ruthenium ion, rhenium ion, osmium ion, chromium ion and iridium ion.

3. The metal complex as claimed in claim 1, wherein M is a ruthenium ion.

4. The metal complex as claimed in claim 1, wherein each of $L_1$, $L_2$ and $L_3$ independently contains a ring system selected from the group consisting of bipyridine and phenanthroline.

5. The metal complex as claimed in claim 1, wherein A is selected from the group consisting of a hexafluorophosphate group, a trifluoroacetate group, a tetrafluoroborate group and a halide ion.

6. The metal complex as claimed in claim 1, wherein the polyhydroxy group is a group of formula (IIa) or (IIb)

—NR—W       (IIa)

—O—W        (IIb)

wherein

W is an organic residue having at least two hydroxy groups and R is hydrogen or $C_1$–$C_5$ alkyl.

7. The metal complex as claimed in claim 6, wherein the polyhydroxy group has a formula —NR—C(CH$_2$OH)$_3$, wherein R is as defined in claim 6.

8. The metal complex as claimed in claim 1, wherein the $C_2$–$C_3$ alkyleneoxy group is an ethyleneoxy group, the $C_2$–$C_3$ alkylenethio group is an ethylenethio group, and the $C_2$–$C_3$ alkyleneamino group is an ethyleneamino group.

9. The metal complex as claimed in claim 1, wherein the metal complex contains 1–30 hydrophilic groups each independently selected from the group consisting of a $C_2$–$C_3$ alkyleneoxy group, a $C_2$–$C_3$ alkylenethio group and a $C_2$–$C_3$ alkyleneamino group.

10. The metal complex as claimed in claim 1, wherein the metal complex is of formula (III):

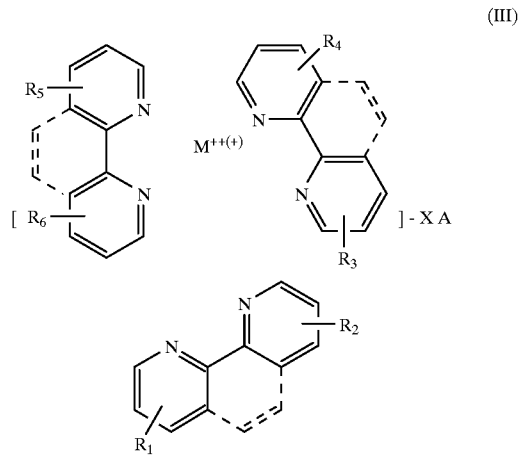

wherein

M, X and A are as defined in claim 1;

one of $R_1$ through $R_6$ is bound to —X; and the remainder of $R_1$ through $R_6$ which are not bound to —X are each independently selected from the group consisting of hydrogen, $C_1$–$C_5$ alkyl and a substituent containing at least one hydrophilic group which is selected from the group consisting of a $C_2$–$C_3$ alkyleneoxy group, a $C_2$–$C_3$ alkylenethio group and a $C_2$–$C_3$ alkyleneamino group, wherein at least one of the remainder of $R_1$ through $R_6$ is the substituent containing the at least one hydrophilic group.

11. The metal complex as claimed in claim 1, wherein the metal complex is of formula (IIIa):

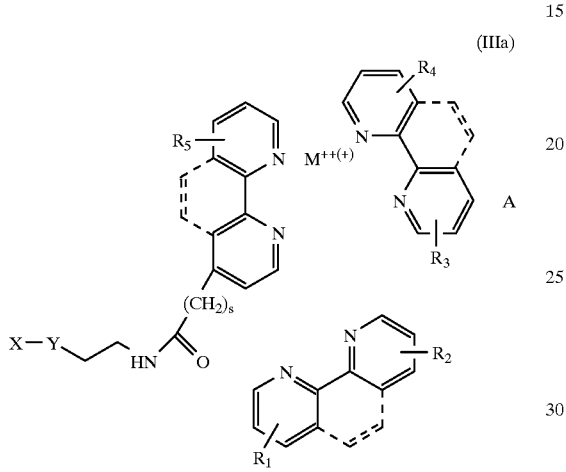

(IIIa)

wherein

M, X and A are as defined in claim 1;

$R_1$ through $R_5$ are each independently selected from the group consisting of hydrogen, $C_1$–$C_5$ alkyl and a substituent containing at least one hydrophilic group which is selected from the group consisting of a $C_2$–$C_3$ alkyleneoxy group, a $C_2$–$C_3$ alkylenethio group and a $C_2$–$C_3$ alkyleneamino group;

s is 0–6; and

Y is a linker having 1–10 hydrophilic groups each independently selected from the group consisting of a $C_2$–$C_3$ alkyleneoxy group, a $C_2$–$C_3$ alkylenethio group and a $C_2$–$C_3$ alkyleneamino group.

12. The metal complex as claimed in claim 1, wherein the metal complex is of formula (IIIb):

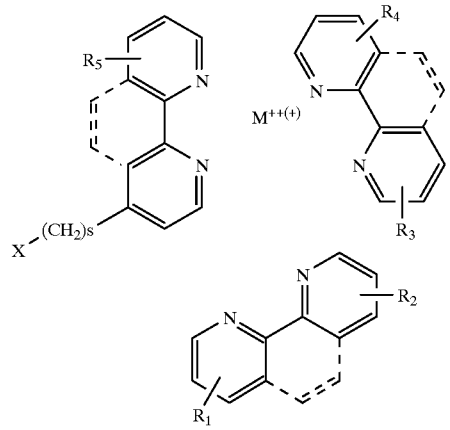

(IIIb)

wherein

M, X and A are as defined in claim 1;

$R_1$ through $R_5$ are each independently selected from the group consisting of hydrogen, $C_1$–$C_5$ alkyl and a substituent containing 1–10 hydrophilic groups each of which is selected from the group consisting of a $C_2$–$C_3$ alkyleneoxy group, a $C_2$–$C_3$ alkylenethio group and a $C_2$–$C_3$ alkyleneamino group, wherein at least one of $R_1$ through $R_5$ is the substituent containing the 1–10 hydrophilic groups; and s is 0–6.

13. The metal complex as claimed in claim 1, wherein the metal complex is of formula (IV):

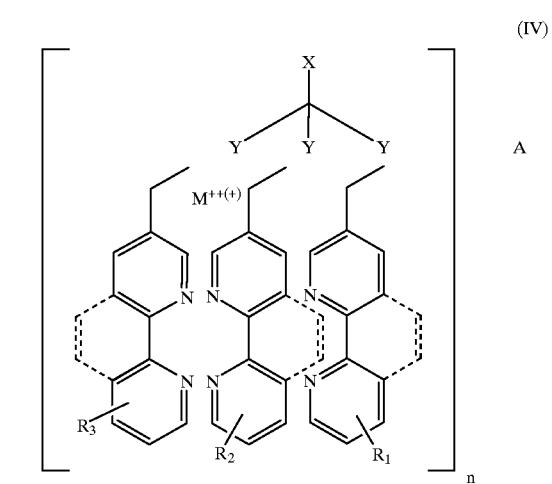

(IV)

wherein

M, Y, X and n are as defined in claim 1;

R$_1$ through R$_3$ are each independently selected from the group consisting of hydrogen, C$_1$–C$_5$ alkyl and a substituent containing at least one hydrophilic group which is selected from the group consisting of a C$_2$–C$_3$ alkyleneoxy group, a C$_2$–C$_3$ alkylenethio group and a C$_2$–C$_3$ alkyleneamino group; and Y is a linker having 1–10 hydrophilic groups each independently selected from the group consisting of a C$_2$–C$_3$ alkyleneoxy group, a C$_2$–C$_3$ alkylenethio group and a C$_2$–C$_3$ alkyleneamino group.

14. The metal complex as claimed in claim 1, wherein the metal complex is of formula (V):

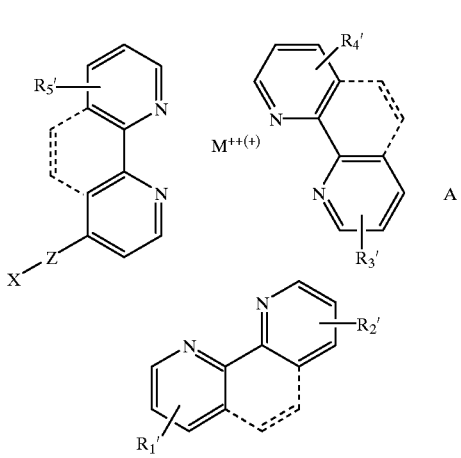

(V)

wherein

M, X and A are as defined in claim 1;

Z is a linker;

R$_1$' through R$_4$' are each independently selected from the group consisting of hydrogen, C$_1$–C$_5$ alkyl and a substituent containing at least one polyhydroxy group, wherein at least one of R$_1$' through R$_4$' is the substituent containing the at least one polyhydroxy group; and R$_5$' is hydrogen or C$_1$–C$_5$ alkyl.

15. The metal complex as claimed in claim 14, wherein the —OH group of the at least one polyhydroxy group is substituted by a hydrophilic group.

16. The metal complex as claimed in claim 15, wherein the hydrophilic group comprises an element of formula (VIa) or (VIb):

—A$_1$—NR—W$_1$(A$_2$—NR—W$_2$)$_n$'     (VIa)

—A$_1$—O—W$_1$(A$_2$—O—W$_2$)$_n$'     (VIb)

wherein

A$_1$ and A$_2$ are each a same or different linker;

W$_1$ and W$_2$ are each a same or different organic residue having at least two hydroxy groups;

R is hydrogen or C$_1$–C$_5$ alkyl; and n' is 0 or the same number as the number of hydroxy groups on W$_1$.

17. A conjugate, comprising a metal complex coupled with a biological substance, wherein the metal complex has the formula:

[M(L$_1$L$_2$L$_3$)]$_n$—X$_m$A wherein

M is a divalent or trivalent metal cation selected from the group consisting of a rare earth metal cation and a transition metal cation;

L$_1$, L$_2$ and L$_3$ are the same or different, and each is a ligand having at least two nitrogen-containing heterocyclic rings, wherein L$_1$, L$_2$ and L$_3$ are bound to the metal cation via nitrogen atoms;

X is a reactive or activatable functional group;

n is 1 to 10;

m is 1 to 6; and

A is at least one negatively charged group, wherein the metal complex contains at least one hydrophilic group selected from the group consisting of a C$_2$–C$_3$ alkyleneoxy group, a C$_2$–C$_3$ alkylenethio group, a C$_2$–C$_3$ alkyleneamino group and a polyhydroxy group, wherein the at least one hydrophilic group is located at at least one of the following locations (a) and (b):

(a) as a substituent or component of a substituent of one of the ligands L$_1$, L$_2$ and L$_3$; and (b) as a linker or component of a linker which links the group X and one of the ligands L$_1$, L$_2$ and L$_3$.

18. The conjugate as claimed in claim 17, wherein the biological substance is selected from the group consisting of biotin, an antibody, an antibody fragment, a nucleic acid, a polypeptide antigen, an immunologically reactive peptide and a hapten.

* * * * *